United States Patent [19]

Niemi et al.

[11] Patent Number: 5,072,854

[45] Date of Patent: Dec. 17, 1991

[54] METHOD FOR TRANSPORTING A CURED ORGANIC OR ORGANOSILOXANE GEL

[75] Inventors: Randolph G. Niemi; Michael R. Strong, both of Midland, Mich.

[73] Assignee: Dow Corning Corporation, Midland, Mich.

[21] Appl. No.: 526,409

[22] Filed: May 18, 1990

[51] Int. Cl.$^5$ .............................................. B67B 3/20
[52] U.S. Cl. ...................................... 222/1; 222/260; 222/261; 222/380
[58] Field of Search .................. 222/1, 256, 261, 262, 222/372, 373, 380, 389, 394, 257, 258, 259, 260; 528/15

[56] References Cited

U.S. PATENT DOCUMENTS

| | | | |
|---|---|---|---|
| 847,760 | 3/1907 | Gates | 222/380 |
| 1,534,859 | 4/1925 | Martin | 222/260 |
| 1,913,592 | 6/1933 | Heffner | 222/380 |
| 2,081,253 | 5/1937 | Serre | 222/260 |
| 3,020,260 | 2/1962 | Nelson | 528/43 |
| 3,419,593 | 12/1968 | Willing | 528/32 |
| 3,445,420 | 5/1969 | Kookootsedes et al. | 528/25 |
| 3,843,601 | 10/1974 | Bruner | 260/46.56 |
| 3,989,667 | 11/1976 | Lee et al. | 528/32 |
| 4,374,967 | 2/1983 | Brown et al. | 528/31 |
| 4,511,620 | 4/1985 | Kroupa et al. | 428/448 |
| 4,608,395 | 8/1986 | Hamade et al. | 528/15 |
| 4,670,530 | 6/1987 | Beck | 528/15 |
| 4,750,962 | 6/1988 | Haygood et al. | 156/249 |
| 4,910,232 | 3/1990 | Arai | 528/32 |

FOREIGN PATENT DOCUMENTS 1-119713  5/1989  Japan .

OTHER PUBLICATIONS

Material News from Dow Corning, New Shock-Absorber Turns 30-mph Crash into 5-mph Bump, Dec. 1969, p. 3.

Primary Examiner—Michael S. Huppert
Assistant Examiner—Philippe Derakshani
Attorney, Agent, or Firm—Robert Spector

[57] ABSTRACT

The present invention is based on the discovery that a cured organic or organosiloxane gel will enter and flow through a conduit to a dispensing location as a coherent, homogeneous portion of material when (1) one end of the conduit is immersed in the gel (2) a sufficient pressure differential is applied between the surface of the gel and the interior of the conduit to cause the gel to enter and at least partially fill a portion of the conduit, and (3) sufficient pressure is then applied within the conduit to cause the gel to flow in the conduit to at least one dispensing location where the gel is withdrawn from the conduit as an integral, homogeneous stream of material.

9 Claims, 2 Drawing Sheets

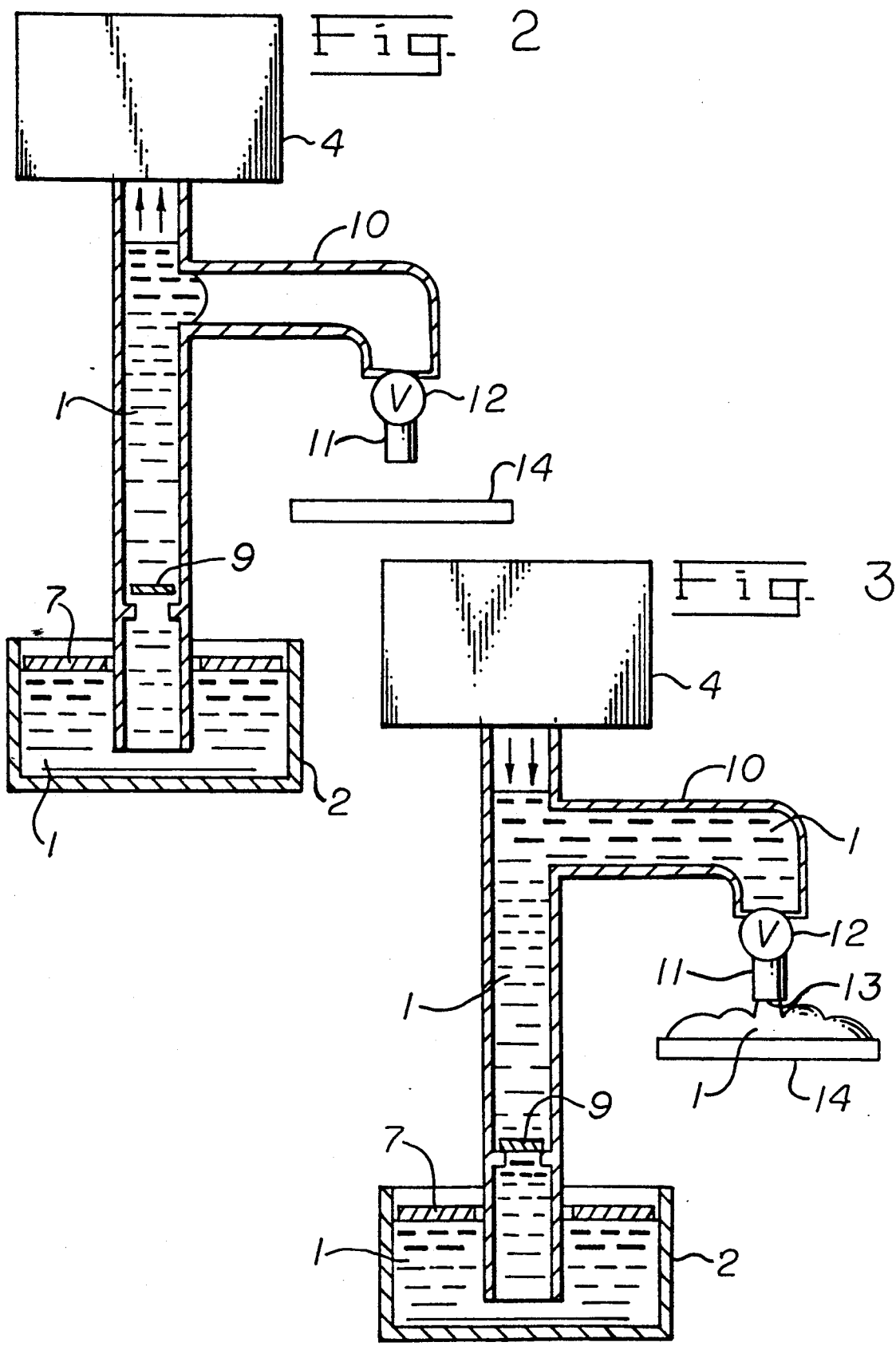

METHOD FOR TRANSPORTING A CURED ORGANIC OR ORGANOSILOXANE GEL

BACKGROUND OF THE INVENTION

1. Field of the Invention

This invention relates to gel type materials. More particularly, this invention relates to a method for transporting cured gels derived from organic or organosiloxane polymer compositions. The gel is transported as an integral, homogeneous mass suitable for use as a coating or encapsulating material.

2. Description of the Prior Art

Organic and organosilicon gels are well known classes of materials. These products are typically lightly crosslinked, unfilled, relatively weak and deformable polymers that do not flow under gravity. The low degree of crosslinking often results in a surface that can be described as sticky or "tacky" to the touch, a property responsible for the excellent adhesion exhibited by the gel to a wide variety of substrates. Gels can also be characterized by their ability to absorb mechanical stresses, to maintain their consistency over a wide temperature range, and to "self-heal" when punctured using a knife or a laboratory spatula.

The elongation value of a typical gel is at least 200 percent.

The unique combination of properties exhibited by gels, particularly organosilicon gels, make them desirable for use as protective coatings and encapsulants on substrates that are exposed to a wide range of temperatures, harsh environments and/or mechanical stresses. Because many gels are excellent electrical insulators, they are used to encapsulate delicate electronic devices such as transistors and integrated circuits and as filling materials for electrical junction boxes and other enclosures containing uninsulated electrical conductors.

Gels are typically prepared by reacting a liquid organic or organosilicon monomer containing functional groups such as vinyl or hydroxyl. Depending upon the type of functional group, the monomer is reacted with free radicals generated by an initiator such as an organic peroxide or ultraviolet light, or with a curing agent containing a plurality of functional groups, such as silicon-bonded hydrogen atoms, that react with the functional groups present on the monomer. To achieve the lightly crosslinked structure that characterizes a gel, when a curing agent is used, a stoichiometric excess of one of the two types of functional groups that react to cure the gel is typically present. The concentration of functional groups is selected to achieve a cured product of the desired consistency and hardness. The hardness of both silicone and organic gels is typically too low to be measured using the Shore A or Shore D durometer scales. The hardness values of some gels can be measured on the Shore 00 scale. A convenient method for defining the hardness of gels is the depth in millimeters to which a probe of specified weight will penetrate the surface of the gel. This value is generally from 1 to about 30 millimeters, preferably from 1 to about 20 millimeters, for a 6.4 mm.-diameter probe weighing 19.5 grams.

In accordance with prior art methods a mixture of the liquid ingredients that react to form the gel is placed on the substrate to be coated or encapsulated. Depending upon the functional groups present on the ingredients, the mixture will cure under ambient conditions, upon heating at temperatures of from about 50° to about 200° C., or when irradiated with ultra-violet light. Depending upon the type of curing reaction and any inhibitors present, heating periods of from several minutes up to an hour or more may be required to cure the composition.

Curing a gel at the location where it is to be applied has at least two disadvantages. Firstly, if the gel is prepared by a platinum-catalyzed hydrosilation reaction or other type of curing reaction requiring a two-part composition to avoid premature curing, specialized equipment to meter, blend and dispense two liquid materials in a specified weight or volume ratio is needed to achieve proper curing and the desired physical properties. The equipment and expertise required to prepare satisfactory gels in a reproducible manner may not be available at the location where the ingredients used to prepare the gel are blended and cured.

Secondly, the use of a liquid curable composition requires providing retainers to maintain the composition at the desired location at least until it cures sufficiently to be non-flowable under the influence of gravity. The need for retainers can present a problem if the gel is used to fill an enclosure such as a electrical junction box, terminal block or connector that contains openings through which wires, cables or other conductors are inserted after the gel is cured.

The tackiness and friability exhibited by cured gels makes it difficult to remove a portion of cured gel from a container in which it is prepared and apply it on the surface of a substrate as a coherent coating in the same manner as one would apply a paint or a grease.

U.S. Pat. No. 4,750,962, which issued to Haygood et al. on June 14, 1988 teaches a method for picking up a cured gel and placing it at a desired location. This patent teaches that gels are difficult to dispense in an automated manner due to their very tacky surface, which causes the gel to adhere to the interior of the dispensing equipment. The method taught in the patent utilizes the relatively weak peel strength of gels by placing a strip or slab of cured gel on a sheet of release paper. One of the disclosed methods for removing the gel from the release paper involves inserting the edge of a blade between the gel and the paper, utilizing the adhesion of the gel to the blade to lift the gel off the paper and transporting the blade containing the adhered gel to the substrate where the gel is to be applied. A second method involves cutting and removing a portion from a layer of gel located on a release paper using a device equipped with means for cutting the gel and applying either vacuum or positive air pressure to the portion of gel cut from the layer. Vacuum is applied to lift the cut portion of gel and retain it in position while the device is moved to the location where the gel is to be dispensed. Positive air pressure is then used to eject the portion of cured gel from the device.

An objective of this invention is to provide a method for transferring a portion of cured silicone or organic gel from the container in which it is cured to the location where it will be applied without fragmenting the gel or otherwise adversely affecting its structure, homogeneity, physical properties or appearance.

SUMMARY OF THE INVENTION

The present invention is based on the discovery that a cured gel will enter and flow through a conduit having inlet and outlet sections as a coherent portion of material when 1) one end of the inlet section of the conduit is immersed in the gel 2) a pressure differential is applied between the surface of the gel outside of the conduit and the interior of the conduit to cause the gel to enter and flow in the inlet section for a distance sufficient to cover the junction with the outlet section of the conduit, and 3) positive pressure is then applied within the inlet section of the conduit to cause the gel to flow in the outlet section to a dispensing location.

BRIEF DESCRIPTION OF THE DRAWINGS

FIGS. 1, 2 and 3 are diagramatic views representing the three major steps of the present method for transporting a cured gel through a conduit to a dispensing location.

DETAILED DESCRIPTION OF THE INVENTION

Figure 1:
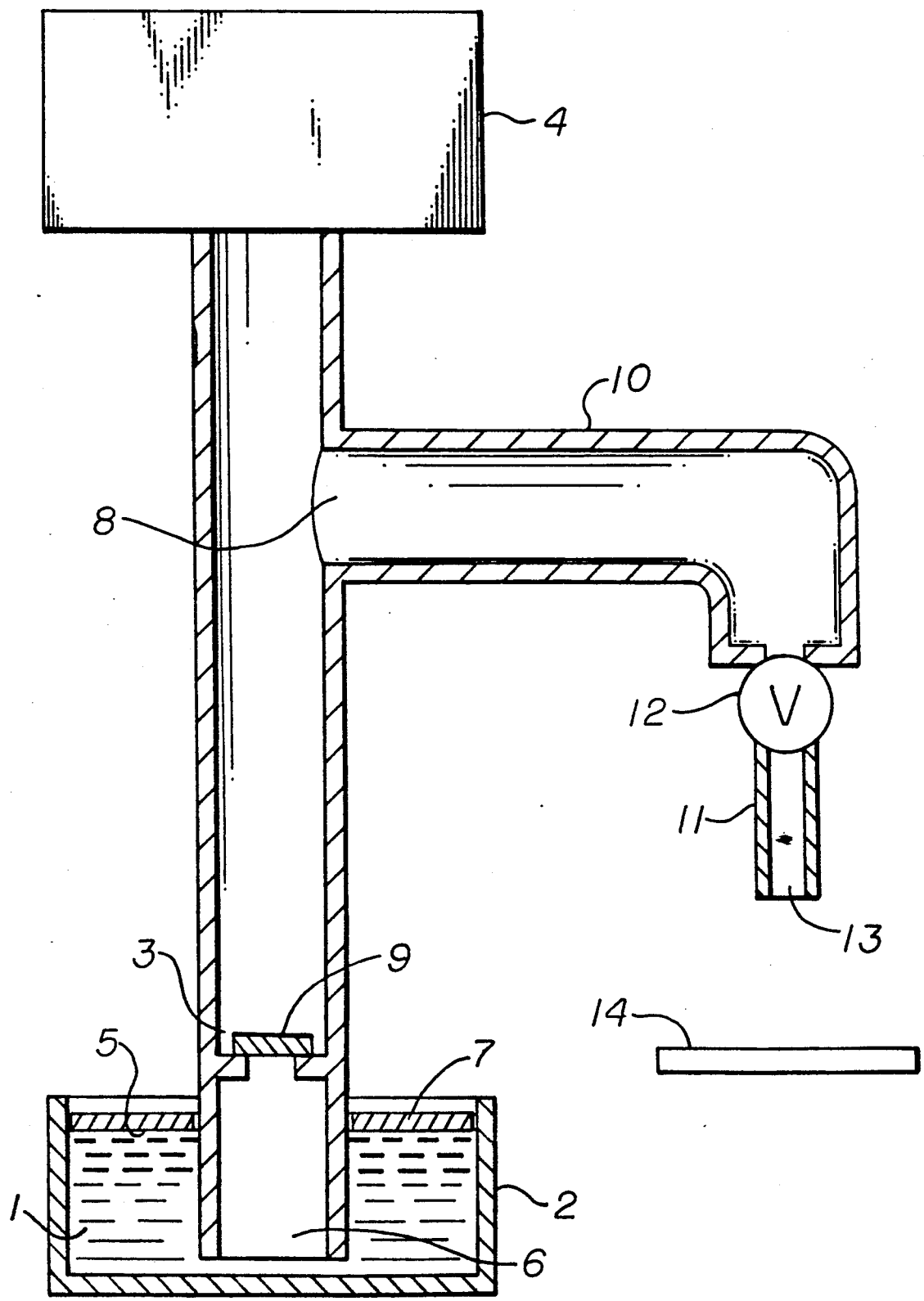

This invention provides a method for transporting as an integral, homogeneous unit at least part of a body of cured gel from a container through a conduit to at least one dispensing location and withdrawing the gel from the conduit at said location, where said conduit comprises (a) an inlet section having a first orifice in continual contact with said body, (b) an outlet section forming a junction with said inlet section and having a second orifice at said dispensing location with control means at said location for controlling the flow of said gel from said second orifice, and (c) isolation means for isolating the portion of said inlet section containing said junction from said first orifice, where said isolation means is activated by positive pressure applied within said conduit in the area of said junction, said method comprising the following sequence of steps:

1. immersing the first orifice of said inlet section in said body and maintaining the orifice at or below the surface thereof,
2. applying a positive pressure differential between the portion of said body external to said first orifice and the portion within said first orifice, said differential being sufficient to cause said gel to enter and flow within said inlet section as a substantially integral homogeneous block of material having a contour corresponding to the contour of said inlet section,
3. maintaining said pressure differential for a period sufficient to cause said block to fill said inlet section and at least a portion of said junction,
4. applying a positive pressure within said inlet section sufficient to activate said isolation means, thereby separating said block from said body and causing said block to flow in the outlet section of said conduit and be transported to said dispensing location, and
5. activating said control means to cause at least a portion of said gel to flow out of said conduit through said outlet orifice as an integral, homogeneous stream of material.

The present method is based on the discovery that cured gels will flow as an integral body within a confined area such as a conduit when subjected to sufficient pressure. The present inventors have found that the device used to apply the pressure must be one that does not mechanically and permanently disrupt the physical structure and homogeneity of the gel. Gear pumps are not suitable for this reason.

The conduit through which the gel flows in accordance with the present method comprises an inlet section that communicates with the container of cured gel and an outlet section containing the location(s) at which the gel is to be dispensed on to the desired substrate. The inlet and outlet sections of the conduit communicate with one another at a junction.

The walls of the conduit are formed from a material that will withstand the pressures required to transport the cured gel and not impede the flow of the gel. To minimize the pressure required to transport the gel the inner surface of the conduit should be smooth and the diameter of the inlet and outlet conduits should be as large as possible based on the desired flow rate of the gel and diameter required at the end of the outlet conduit. In a preferred embodiment the diameters of the inlet and outlet conduits are 2.5 and 0.25 inches (6.4 and 0.6 cm.) respectively.

The pressure differentials required to cause a coherent portion of the cured gel to enter and be transported through the inlet and outlet sections of the conduit are generated using a pressure/vacuum source such as a piston or equivalent device capable of (a) compressing a portion of the air or other gas confined in the conduit through which the gel travels and (b) creating a partial vacuum within the conduit. In place of a piston one can use a source of compressed gas such as nitrogen or air and vacuum source such as a vacuum pump.

The pressure differential required to force the cured gel to flow from the container in which it was cured into the inlet section of the conduit and through the conduit to one or more dispensing positions at the end of the outlet section of the conduit is a function of a number of parameters, including but not limited to the viscosity of the polymer(s) used to prepare the gel, the hardness of the gel, the extent to which the gel is crosslinked and the diameter and length of the inlet and outlet sections. For preferred gels of this invention the pressure is typically from about 50 to 500 psig (450 to 3600 kPa.), recognizing that higher pressures may exist at various locations in the inlet and outlet sections.

One class of preferred devices for transporting cured gels in accordance with the present invention are referred to as positive displacement piston pumps and are available in a variety of designs and capacities.

Referring to the accompanying drawings, FIG. 1 represents the first step of the present method, during which a portion of cured gel (1) is made to flow from the container (2) in which it was prepared into the inlet section (3) of the conduit. This is accomplished by creating a negative pressure differential, relative to atmospheric pressure, in the inlet section of the conduit using a pressure/vacuum source (4). In addition to the negative pressure differential resulting from the creation of a partial vacuum in the inlet section some gels require application of superatmospheric pressure to the surface (5) of the gel outside of the inlet orifice to cause the gel to flow into the conduit. This is also referred to as applying a positive pressure differential to the surface of the gel outside of the conduit.

The pressure differential required to cause the gel to flow from the container into the inlet section of the conduit can be generated by placing the orifice (6) of the inlet section on or below the surface of the cured gel in a partially filled, pressure resistant container, sealing the container and injecting a compressed gas such into the space above the gel surface while creating a partial vacuum in the inlet section of the conduit.

Alternatively, the pressure required to force the gel to flow into the conduit can be generated by covering the surface of the gel with a device referred to in the art as a follower plate (7). The plate forms a seal between itself and the inner wall of the container of cured gel. In one embodiment the plate also contains the inlet orifice of the conduit. The pressure that forces the follower plate against the surface of the gel can be generated by injecting a compressed gas such as air into a sealed container of gel or by attaching the follower plate to a piston operated by a pressurized gas or fluid.

It will be understood that to increase the efficiency of the pump and avoid entrapment of air in the conduits the orifice of the inlet portion of the conduit must remain in contact with the surface of the body of cured gel in the container throughout the process of transporting the gel.

The amount of cured gel that is drawn into the conduit during the first step of the present method should be sufficient to at least partially fill the junction (8) between the inlet and outlet sections of the conduit. The amount of gel drawn into the junction area should be sufficient to provide the desired amount of gel at the dispensing location(s) (11) during the following pressurization step. To maximize the quantity of gel that is transported to the dispensing location during the pressurization step of the present method, the body of gel in the conduit should extend as far as possible beyond the junction of the inlet and outlet sections of the conduit in the direction of the source of the pressure (4) used to transport the gel in the conduit.

Referring now to FIG. 2 of the drawings, when the desired amount of gel has been drawn into the conduit from the container or other supply source the orifice of the inlet section is sealed off from the remainder of the conduit using a pressure operated check valve (9) or equivalent device. The inlet section is then pressurized sufficiently to cause the gel located in the junction of the inlet and outlet sections to flow in the outlet section (10) of the conduit to the dispensing location(s) (11). It should be understood that the portion of gel entering the outlet section during this step of the present method was initially located between the junction of the inlet and outlet sections and the pressure source in the inlet section. The check valve (9) or other isolation device prevents the gel in the inlet section of conduit from flowing back into the container (2) in which it was stored prior to entering the conduit.

Referring now to FIG. 3 of the drawings, each dispensing location is equipped with a control means (12) that allows the gel to flow out of the orifice of the outlet section (13) on to a suitable substrate (14) as an integral, homogeneous stream.

Cured gels that can be transported in accordance with the present method typically exhibit a hardness that can be expressed in terms a penetration value, which is a measure of the distance that a probe of a specified weight, shape and surface area will depress or penetrate below the surface of the gel. For the present gels this value is typically from 1 to about 30 mm., preferably from 1 to 20 mm. For the purposes of this invention, penetration values are measured using a Universal Penetrometer available as Catalog No. 73,150 from the Precision Scientific Company. The standard cones supplied with the penetrometer are replaced with a brass head 6.35 mm in diameter and 4.762 mm high, having a flat bottom surface and rounded edges. The total weight of the shaft and head is 19.5 grams.

Gels with penetration values less than 1 mm. are typically too crosslinked and non-conformable to retain coherency during transport in a conduit in accordance with the present method, while gels with penetration values greater than 30 mm. are too flowable under the influence of gravity to be useful as coatings and encapsulants.

Organic polymers suitable for preparing cured gels that can be transported in accordance with the present method include but are not limited to polyacrylic acid, polymethacrylic acid, polyacrylonitrile, polyurethanes, polysulfones, polyesters and polyamides. Organic polymer gels are disclosed in Japanese Patent No. 1,119,713 which issued on May 11, 1989.

Compositions for preparing cured organosiloxane gels typically include at least one polyorganosiloxane that is preferably substantially linear and contains two or more groups that will react with groups on the curing agent to form a covalent chemical bond. The groups on the polyorganosiloxane are typically silanol or silicon-bonded alkenyl radicals, and the groups on the curing agent are typically silicon bonded hydrogen, methoxy, ethoxy, or other silicon-bonded hydrolyzable group such as acetoxy. Depending upon the type of curable composition used to prepare the gel, the location of these reactive groups can be interchanged between the polyorganosiloxane and the curing agent. The curing agent contains at least two, preferably at least three, of these reactive groups. The reactive groups on the polyorganosiloxane are preferably located at least at the terminal positions of the molecule.

Preferred curable organosiloxane compositions are curable by a platinum-catalyzed hydrosilation reaction or upon irradiation with ultraviolet light. Compositions curable by a hydrosilation reaction comprise one or more liquid polyorganosiloxanes containing alkenyl radicals located at the terminal positions of each molecule, an organohydrogensiloxane containing an average of at least two silicon-bonded hydrogen atoms per molecule in an amount sufficient to cure said composition sufficiently to form a gel, and an amount of a platinum-containing hydrosilation catalyst in an amount sufficient to promote curing of said composition. The molar ratio of silicon bonded hydrogen atoms to alkenyl radicals is preferably from 0.2 to about 0.7, and the alkenyl radicals are most preferably vinyl.

Compositions suitable for use in preparing organosiloxane gels are described in U.S. Pat. No. 3,020,260, which issued to Nelson on Feb. 6, 1962 and U.S. Pat. No. 4,374,967, which issued to Paul Brown et al. on Feb. 22, 1983.

The ingredients of preferred curable organosiloxane compositions will now be discussed in detail.

The polyorganosiloxane ingredient of the present compositions can be represented by the general formula

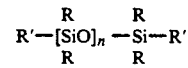

where R represents a monovalent hydrocarbon radical or a monovalent halohydrocarbon radical, R' represents an alkenyl radical, and n represents a degree of polymerization equivalent to a viscosity of from 1 to about 40 Pa·s at 25° C.

The radical represented by R can contain from 1 to about 20 carbon atoms and is free of ethylenic unsaturation. A range of from 1 to 10 carbon atoms is preferred. Most preferably R is methyl, phenyl or 3,3,3-trifluoropropyl and R' is vinyl. These preferences are based on the availability of the reactants typically used to prepare the polyorganosiloxane.

The reaction mixture can contain a single polyorganosiloxane ingredient. Alternatively two or more polyorganosiloxanes of different molecular weights can be present.

The polyorganosiloxane ingredient is cured to form an elastomeric gel by a hydrosilation reaction with the silicon-bonded hydrogen atoms present on the curing agent. The curing agent contains from as few as four silicon atoms per molecule up to an average of 20 or more, and can have a viscosity of up to 10 Pa·s or higher at 25° C. The repeating units that can be present in this ingredient include but are not limited to $HSiO_{1.5}$, $R''HSiO$ and/or $R''_2HSiO_{0.5}$ in addition to one or more of monoorganosiloxy, diorganosiloxane, triorganosiloxy and $SiO_{4/2}$ units. In these formulae $R''$ is a monovalent hydrocarbon or halocarbon radical as defined for the R radical of the polyorganosiloxane.

Alternatively the organohydrogensiloxane can be a cyclic compound containing diorganosiloxane and organohydrogensiloxane units or a compound of the formula $Si(OSiR''_2H)_4$.

Most preferably $R''$ is methyl and the curing agent is a linear trimethylsiloxy terminated dimethylsiloxane-/methylhydrogensiloxane copolymer containing an average of from 10 to about 50 repeating units per molecule of which from 3 to 5 are methylhydrogensiloxane.

Hydrosilation reactions are typically conducted in the presence of a catalyst that is a platinum group metal or a compound of such a metal. Platinum compounds such as hexachloroplatinic acid, and particularly complexes of these compounds with relatively low molecular weight vinyl-containing organosiloxane compounds are preferred catalysts because of their high activity and compatibility with the organosiloxane reactants. These complexes are described in U.S. Pat. No. 3,419,593 that issued to David N. Willing on Dec. 31, 1968. Complexes with low molecular weight organosiloxanes wherein the silicon bonded hydrocarbon radicals are vinyl and either methyl or 3,3,3-trifluoropropyl are particularly preferred because of their ability to catalyze a rapid curing of the elastomer at temperatures of at least about 70° C.

The platinum containing catalyst can be present in an amount equivalent to as little as one part by weight of platinum per one million parts of curable composition. Catalyst concentrations equivalent to from 5 to 50 parts of platinum per million of curable composition are preferred to achieve a practical curing rate. Higher concentrations of platinum provide only marginal improvements in curing rate, and are therefore economically unattractive, particularly when the preferred catalysts are used.

Mixtures of the aforementioned polyorganosiloxane curing agent and platinum-containing catalysts may begin to cure at ambient temperature. When it is desired to increase the storage stability of these compositions or obtain a longer working time or "pot life", the activity of the catalyst under ambient conditions can be retarded or suppressed by the addition of a suitable inhibitor.

Known platinum catalyst inhibitors include the acetylenic compounds disclosed in U.S. Pat. No. 3,445,420, which issued on May 20, 1969 to Kookootsedes et al. Acetylenic alcohols such as 2-methyl-3-butyn-2-ol constitute a preferred class of inhibitors that will suppress the activity of a platinum-containing catalyst at 25° C. Compositions containing these catalysts typically require heating at temperatures of 70° C. or above to cure at a practical rate.

When it desired to increase the pot life of a curable composition under ambient conditions, this can be accomplished using an ethylenically unsaturated siloxane of the type described in U.S. Pat. No. 3,989,667, which issued on Nov. 2, 1876 to Lee and Marko. Cyclic methylvinylsiloxanes are preferred.

Inhibitor concentrations as low as one mole of inhibitor per mole of platinum will in some instances impart satisfactory storage stability and cure rate. In other instances inhibitor concentrations of up to 500 or more moles of inhibitor per mole of platinum are required. The optimum concentration for a given inhibitor in a given composition can readily be determined by routine experimentation and does not constitute part of this invention.

Preferred organosiloxane gel compositions that cure when irradiated with ultraviolet light typically include a polyorganosiloxane containing at least two ethylenically unsaturated groups and a photoinitiator that generates free radicals in the presence of ultraviolet light. Examples of ethylenically unsaturated groups that can be present in compositions include but are not limited to acryloxy, methacryloxy, acrylamido, and a combination of alkenyl radicals such as vinyl with mercapto groups as the photoinitiator.

EXAMPLES

The following examples are intended to describe preferred embodiment of the present invention and should not be interpreted as limiting the scope of the invention as defined in the accompanying claims. Unless otherwise specified all parts and percentages disclosed in the examples are by weight and viscosities and penetration values were measured at 25° C.

Two curable organosiloxane gel compositions were prepared by blending the following ingredients to homogeneity.

Composition 1

98.70 parts of a dimethylvinylsiloxy terminated polydimethylsiloxane having a viscosity of about 0.4 Pa·s at 25° C.;

0.85 part of a trimethylsiloxy terminated polydiorganosiloxane having an average of five methylhydrogensiloxane units and three dimethylsiloxane units per molecule and containing from 0.7 to 0.8 weight percent of silicon-bonded hydrogen atoms;

0.4 part of a reaction product of hexachloroplatinic acid and sym-tetramethyldivinyldisiloxane that has been diluted with a liquid dimethylvinylsiloxy terminated polydimethylsiloxane in an amount sufficient to achieve a platinum content of 0.7 weight percent; and 0.05 part of cyclic methylvinylsiloxanes.

The resultant mixture was stored for 24 hours at a temperature of 21° C., during which time it cured to form a transparent gel having a penetration value of 4 mm, measured using a 19.5 gram probe of the type described in the preceding specification.

Composition 2

98.85 parts of a dimethylvinylsiloxy endblocked polydimethylsiloxane having a viscosity of about 0.4 Pa·s at 25° C.

0.7 part of a trimethylsiloxy terminated polydiorganosiloxane having an average of five methylhydrogensiloxane units and three dimethylsiloxane units per molecule and containing from 0.7 to 0.8 weight percent of silicon-bonded hydrogen atoms;

0.4 part of a reaction product of hexachloroplatinic acid and sym-tetramethyldivinyldisiloxane that has been diluted with a liquid dimethylvinylsiloxy terminated polydimethylsiloxane in an amount sufficient to achieve a platinum content of 0.7 weight percent;

0.05 part of cyclic methylvinylsiloxanes; and a trace amount of a blue dye.

The resultant mixture was stored for 72 hours at a temperature of 21° C., during which time it cured to form a transparent gel having a penetration value of 6-6.5 mm, measured using a 19.5 gram probe of the type described in the preceding specification. This penetration value is considered the upper limit for a gel capable of maintaining its integrity under ambient conditions. Softer gels would be expected to flow under the influence of gravity.

The device used to transport the cured gels was a piston type pump available as model 204-287 from Graco, Inc. The ratio of the diameter of the piston in the air driven motor to the piston in the pump section was 20:1. The pump was equipped with a check valve located near the inlet orifice and a pneumatically operated ram unit connected to a circular follower plate of the same diameter as the inner diameter of the container holding the cured gel. The outer rim of the follower plate formed a seal with the inner wall of the gel container to prevent the gel from flowing between the follower plate and the container wall. The 2.5 inch (6.4 cm.)-diameter circular orifice of the inlet section of the pump was located in the center of the follower plate.

The outlet of the pump was connected to a 6 inch (15 cm.)-long section of 0.25 inch (0.6 cm.)-diameter stainless steel pipe that terminated in a valve attached to a tapered circular nozzle having an inlet diameter of 0.25 inch (0.6 cm.) and an outlet diameter of 0.06 inch (0.15 cm.). This combination of pipe, valve and nozzle attached to the outlet of the pump is equivalent to the outlet section of the conduit described in connection with the present method. The pressure in the conduit was measured by means of a gauge located at the junction of the inlet and outlet sections of the conduit.

During operation of the pump the follower plate was placed on the surface of the cured gel and the ram unit was pressurized to provide a pressure of 70 psig (587 kPa) against the surface of the gel. This forced the gel into the orifice of the inlet section of the pump, equivalent to the inlet section of the conduit described earlier in this specification. The presence of gel at this location was required to maintain the prime on the pump.

During the suction cycle the piston of the pump was moving in a direction away from the inlet orifice, causing the check valve in the inlet conduit to move into the open position and allowing a portion of the gel in the container to be drawn up into the conduit and flow beyond the junction between the inlet and outlet sections of the conduit.

During the pressure portion of the cycle the direction of piston travel was reversed, forcing the check valve in the inlet section to close and seal off the inlet orifice from the remainder of the conduit. The resultant increase in pressure within the inlet section forced the gel in the area between the pressure source and the junction of the inlet and outlet sections to enter the outlet section and flow to the dispensing valve located at the end of the outlet section.

When the dispensing valve was opened the gel emerged from the nozzle as a continuous length of homogeneous translucent material. A sample of the gel from both compositions appeared transparent when pressed between two glass plates.

The pressure supplied to the pump (P1), the pressure applied to the gel (P2), measured at the junction of the inlet and outlet sections of the conduit, and the flow rate of the gel at the dispensing location (in grams per minute) are recorded in Table 1.

TABLE 1

| P1 (kPa) | P2 (kPa) | Gel Flow Rate (g/minute) |
| --- | --- | --- |
| Composition 1 | | |
| 173 | 449 | 4.65 |
| 207 | 1898 | 18.24 |
| 242 | 2174 | 26.37 |
| 276 | 2864 | 50.73 |
| 311 | 4244 | 130.28 |
| 380 | 6141 | 287.88 |
| Composition 2 | | |
| 173 | 449 | 30.87 |
| 207 | 1484 | 286.41 |
| 242 | 2243 | 1348.65 |
| 311 | 3623 | 3028.08 |

The data in Table 1 demonstrate the ability of the present method to transport cured gels of substantially different hardness, as determined by their penetration values.

That which is claimed is:

1. A method for transporting as an integral homogeneous unit at least part of a body of cured gel from a container through a conduit to at least one dispensing location, where said conduit comprises (a) an inlet section having a contour and a first orifice in continual contact with said body, (b) an outlet section forming a junction with said inlet section and having an second orifice at said dispensing location with control means at said location for controlling the flow of said gel from said second office, and (c) isolation means for isolating the portion of said inlet section containing said junction from said first orifice, where said isolation means is activated by positive pressure applied within said conduit in the area of said junction, said method comprising the following sequence of steps:

1) immersing the first orifice of said inlet section in said body and maintaining the orifice at or below the surface thereof, 2) creating a pressure differential between a first portion of said body external to said first office and a second portion within said first orifice by applying superatmospheric pressure to the exposed surface of said first portion while creating a partial vacuum in said inlet section, said differential being from 50 to 500 p.s.i. and sufficient to cause said gel to enter and flow within said inlet section as a substantially integral homogeneous block of material having a contour corresponding to the contour of said inlet section, 3) maintaining said pressure differential for a period sufficient to cause said block to fill said inlet section and at least a portion of said junction, 4) applying a positive pressure within said inlet section sufficient to activate said isolation means, thereby separating said block from said body and causing said block to flow in the outlet section of said conduit and be transported to said dispensing location, and 5) activating said control means to cause at least a portion of said gel to flow out of said conduit through said outlet orifice as an integral, homogeneous stream of material.

2. A method according to claim 1 where said pressure differential and said positive pressure are generated using a piston pump and the chamber of said pump forms the inlet section of said conduit.

3. A method according to claim 1 where said gel is an organosiloxane gel.

4. A method according to claim 1 where said gel is transparent, non-flowing under the influence of gravity, and exhibits a penetration of from 1 to 30 millimeters using a 19.5 gram probe having a diameter of 6.4 millimeters.

5. A method according to claim 3 where said gel is cured by irradiation with ultraviolet light.

6. A method according to claim 3 where said gel is cured by a platinum-catalyzed hydrosilation reaction.

7. A method according to claim 6 where said gel is prepared from a composition comprising A. a liquid polyorganosiloxane where at least two of the silicon-bonded hydrocarbon radicals in each molecule are alkenyl radicals, B. an organohydrogensiloxane containing silicon-bonded hydrocarbon radicals and an average of at least two silicon-bonded hydrogen atoms per molecule, the amount of said organohydrogensiloxane being sufficient to cure said composition and C. an amount of a platinum-containing hydrosilation catalyst in an amount sufficient to promote curing of said composition.

8. A method according to claim 7 where the silicon-bonded hydrocarbon radicals other than said alkenyl radicals that are present on said polyorganosiloxane and said polyorganohydrogensiloxane are selected from methyl, phenyl and 3,3,3-trifluoropropyl.

9. A method according to claim 8 where said hydrocarbon radicals are methyl and said alkenyl radical is vinyl.

* * * * *